United States Patent

Clough et al.

Patent Number: 5,221,691
Date of Patent: Jun. 22, 1993

[54] FUNGICIDES AROMATIC OXIME AMIDES

[75] Inventors: John M. Clough, Marlow; Christopher R. A. Godfrey, Bracknell; Paul J. de Fraine; Ian R. Matthews, both of Wokingham, all of England

[73] Assignee: Imperial Chemical Industries PLC, Millbank, Great Britain

[21] Appl. No.: 827,236

[22] Filed: Jan. 29, 1992

[30] Foreign Application Priority Data

Jan. 30, 1991 [GB] United Kingdom ............... 9102038
Jul. 14, 1991 [GB] United Kingdom ............... 9117530

[51] Int. Cl.$^5$ ............... A61K 31/165; C07C 255/00; C07C 233/00; C07C 235/00
[52] U.S. Cl. ............... 514/619; 514/621; 514/622; 558/414; 564/163; 564/166; 564/167
[58] Field of Search ............... 564/163, 166, 167; 514/619, 621, 622; 558/414

[56] References Cited

U.S. PATENT DOCUMENTS 5,055,471 10/1991 de Fraine et al. ............... 544/205

FOREIGN PATENT DOCUMENTS 0398692 11/1990 European Pat. Off. .

Primary Examiner—Mukund J. Shah
Assistant Examiner—Y. N. Gupta
Attorney, Agent, or Firm—William E. Dickheiser

[57] ABSTRACT

Fungicidal compounds having the formula (I):

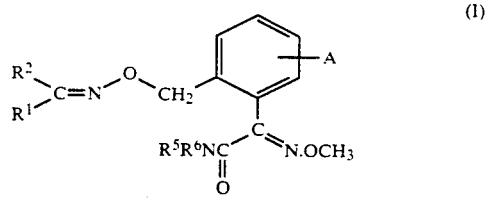

and stereoisomers thereof, wherein A is hydrogen, halo, hydroxy, $C_{1-4}$ alkyl, $C_{1-4}$ alkoxy, $C_{1-4}$ haloalkyl, $C_{1-4}$ haloalkoxy, $C_{1-4}$ alkylcarbonyl, $C_{1-4}$ alkoxycarbonyl, phenoxy, nitro or cyano; $R^1$ and $R^2$, which may be the same or different, are hydrogen, optionally substituted alkyl, optionally substituted cycloalkyl, optionally substituted heterocyclylalkyl, optionally substituted cycloalkylalkyl, optionally substituted aralkyl, optionally substituted aryloxyalkyl, optionally substituted heterocyclyloxyalkyl, optionally substituted alkenyl, optionally substituted alkynyl, optionally substituted alkoxy, optionally substituted aryl, optionally substituted heterocyclyl, optionally substituted aryloxy, optionally substituted heterocyclyloxy, nitro, halo, cyano, $-NR^3R^4$, $-CO_2R^3$, $-CONR^3R^4$, $-COR^3$, $-S(O)_nR^3$ wherein n is 0, 1 or 2, $(CH_2)_mPO(OR^3)_2$ wherein m is 0 or 1, or $R^1$ and $R^2$ join to form a carbocyclic or heterocyclic ring system; $R^3$ and $R^4$, which are the same or different, are hydrogen, optionally substituted alkyl, optionally substituted aralkyl, optionally substituted alkenyl, optionally substituted alkynyl, optionally substituted aryl or optionally substituted heteroaryl, or $R^3$ and $R^4$ join to form an optionally substituted heterocyclic ring; and $R^5$ and $R^6$ are independently hydrogen or $C_{1-4}$ alkyl.

7 Claims, No Drawings

FUNGICIDES AROMATIC OXIME AMIDES

This invention relates to derivatives of O-methyl oxyiminoacetamide useful as fungicides, insecticides and miticides, to processes for preparing them, to compositions containing them, and to methods of using them to combat fungi, especially fungal infections of plants, and to kill or control insects and mites.

According to the present invention there is provided a compound having the formula (I), and stereoisomers thereof, wherein A is hydrogen, halo, hydroxy, $C_{1-4}$ alkyl, $C_{1-4}$ alkoxy, $C_{1-4}$ haloalkyl, $C_{1-4}$ haloalkoxy, $C_{1-4}$ alkylcarbonyl, $C_{1-4}$ alkoxycarbonyl, phenoxy, nitro or cyano; $R^1$ and $R^2$, which may be the same or different, are hydrogen, optionally substituted alkyl, optionally substituted cycloalkyl, optionally substituted heterocyclylalkyl (particularly optionally substituted heteroarylalkyl), optionally substituted cycloalkylalkyl, optionally substituted aralkyl, optionally substituted aryloxyalkyl, optionally substituted heterocyclyloxyalkyl (particularly optionally substituted heteroaryloxyalkyl), optionally substituted alkenyl, optionally substituted alkynyl, optionally substituted alkoxy, optionally substituted aryl, optionally substituted heterocyclyl (particularly optionally substituted heteroaryl), optionally substituted aryloxy, optionally substituted heterocyclyloxy (particularly optionally substituted heteroaryloxy), nitro, halo, cyano, $-NR^3R^4$, $-CO_2R^3$, $-CONR^3R^4$, $-COR^3$, $-S(O)_nR^3$ wherein n is 0, 1 or 2, $(CH_2)_mPO(OR^3)_2$ wherein m is 0 or 1, or $R^1$ and $R^2$ join to form a carbocyclic or heterocyclic ring system; $R^3$ and $R^4$, which are the same or different, are hydrogen, optionally substituted alkenyl, optionally substituted aralkyl, optionally substituted alkenyl, optionally substituted alkynyl, optionally substituted aryl or optionally substituted heteroaryl, or $R^3$ and $R^4$ join to form an optionally substituted heterocyclic ring; and $R^5$ and $R^6$ are independently hydrogen or $C_{1-4}$ alkyl.

The compounds of the invention contain at least two carbon-nitrogen double bonds and are sometimes obtained in the form of mixtures of geometric isomers. However these mixtures can be separated into individual isomers and this invention embraces such isomers and mixtures thereof in all proportions.

The individual isomers which result from the unsymmetrically substituted double bond of the oxime groups are identified by the commonly used terms "E" and "Z". These terms are defined according to the Cahn-Ingold-Prelog system which is fully described in the literature (see, for example, J. March, "Advanced Organic Chemistry", 3rd edition, Wiley-Interscience, page 109 et seq).

For the carbon-nitrogen double bond of the oxyiminoacetamide group, usually one isomer is more active fungicidally than the other, the more active isomer usually being the (E)-isomer. These (E)-isomers form a preferred embodiment of this invention.

Halo includes fluoro, chloro, bromo and iodo.

Alkyl and the alkyl moieties of alkoxy, aralkyl and aryloxyalkyl can be in the form of straight or branched chains and, unless otherwise stated, suitably contain from 1 to 6 carbon atoms. Examples are methyl, ethyl, iso-propyl and tert-butyl. Optional substituents include halo (especially chloro and fluoro), cyano, hydroxy, $C_{1-4}$ alkoxy and $C_{1-4}$ alkoxy($C_{1-4}$)alkoxy. Examples of substituted alkyl and substituted alkoxy are trifluoromethyl and trifluoromethoxy.

Cycloalkyl is suitably $C_{3-6}$ cycloalkyl, for example cyclopropyl or cyclohexyl, and cycloalkylalkyl is suitably $C_{3-6}$ cycloalkyl($C_{1-4}$)alkyl, for example 1- or 2-cyclopropylethyl. Optional substituents include halo, hydroxy and $C_{1-4}$ alkoxy.

Alkenyl and alkynyl suitably contain from 2 to 6 carbon atoms, typically 2 to 4 carbon atoms, in the form of straight or branched chains. Examples are ethenyl, allyl and propargyl. Substituted alkenyl and alkynyl groups include optionally substituted aryl- and heteroarylalkenyl (especially optionally substituted aryl- and heteroaryl($C_{2-4}$)alkenyl and, particularly, optionally substituted phenylethenyl) and arylalkynyl.

Aryl and the aryl moieties of aralkyl, arylalkenyl, arylalkynyl, aryloxy and aryloxyalkyl include phenyl and naphthyl.

The carbocyclic or heterocyclic ring system which $R^1$ and $R^2$ may form together is suitably a $C_{4-10}$ (typically $C_{5-10}$) aliphatic, aromatic or mixed aliphatic/aromatic carbocyclic ring system, for example cyclopentyl, cyclohexyl, cyclohexadienonyl and such groups carrying one or two optionally substituted fused benzene rings and/or substituents such as methyl; or it may be a 4- to 10-membered (typically 5- to 10-membered) heterocyclic ring system, for example tetrahydropyranyl.

The term heterocyclyl includes aromatic heterocyclic groups, referred to as heteroaryl groups. Heterocyclyl and the heterocyclyl moieties of other groups, such as heterocyclylalkyl, are typically 5- or 6-membered aromatic or non-aromatic rings containing one or more O, N or S heteroatoms which may be fused to one or more other aromatic or heteroaromatic or other heterocyclic rings, such as a benzene ring. Examples are thienyl, furyl, pyrrolyl, isoxazolyl, oxazolyl, pyrazolyl, imidazolyl, triazolyl, thiazolyl, pyridyl, pyrimidinyl, pyrazinyl, pyridazinyl, triazinyl, benzofuryl, benzothienyl, dibenzofuryl, benzothiazolyl, benzoxazolyl, indolyl, quinolinyl and quinoxalinyl groups and, where appropriate, N-oxides thereof.

The optionally substituted heterocyclic ring which $R^3$ and $R^4$ may join to form is suitably a 5 to 7 membered hetero ring having 1 to 3 heteroatoms which are independently selected from O, S or N, and having 1 to 3 substituents which are, for example, halogen, cyano, nitro, $C_{1-6}$ alkyl, $C_{1-6}$ alkoxy, $C_{1-6}$ alkylthio, or a heterocyclic ring such as described in the previous paragraph. Examples are pyrrolidine, piperidine, morpholine, thiomorpholine, piperazine, hexamethyleneimine, tetrahydroquinoline, tetrahydroisoquinoline and 2,3-dihydro-1,4-benzoxazine.

Substituents which may be present in optionally substituted aryl and heterocyclyl, including heteroaryl, moieties include one or more of the following: halo, hydroxy, mercapto, $C_{1-4}$ alkyl (especially methyl and ethyl), $C_{2-4}$ alkenyl (especially allyl), $C_{2-4}$ alkynyl (especially propargyl), $C_{1-4}$ alkoxy (especially methoxy), $C_{2-4}$ alkenyloxy (especially allyloxy), $C_{2-4}$ alkynyloxy (especially propargyloxy), halo($C_{1-4}$)alkyl (especially trifluoromethyl), halo($C_{1-4}$)alkoxy (especially trifluoromethoxy), $C_{1-4}$ alkylthio (especially methylthio), hydroxy($C_{1-4}$)alkyl, $C_{1-4}$ alkoxy($C_{1-4}$)alkyl, $C_{1-4}$ alkoxy($C_{1-4}$)alkoxy, $C_{3-6}$ cycloalkyl, $C_{3-6}$ cycloalkyl($C_{1-4}$)alkyl, optionally substituted aryl (especially optionally substituted phenyl), optionally substituted heteroaryl (especially optionally substituted pyridyl or pyrimidinyl), optionally substituted aryloxy (especially optionally substituted phenoxy), optionally substituted heteroaryloxy (especially optionally substituted pyridyloxy or pyrimidinyloxy), optionally substituted aryl($C_{1-4}$)alkyl (especially optionally substituted benzyl, optionally substituted phenethyl and optionally substituted phenyl n-propyl) in which the alkyl moiety is optionally substituted with hydroxy, optionally substituted heteroaryl($C_{1-4}$)alkyl (especially optionally substituted pyridyl- or pyrimidinyl($C_{1-4}$)alkyl), optionally substituted aryl($C_{2-4}$)alkenyl (especially optionally substituted phenylethenyl), optionally substituted heteroaryl($C_{2-4}$)alkenyl (especially optionally substituted pyridylethenyl or pyrimidinylethenyl), optionally substituted aryl($C_{1-4}$)alkoxy (especially optionally substituted benzyloxy), optionally substituted heteroaryl($C_{1-4}$)alkoxy (especially optionally substituted pyridyl-, or pyrimidinyl($C_{1-4}$)alkoxy), optionally substituted aryloxy($C_{1-4}$)alkyl (especially phenoxymethyl), optionally substituted heteroaryloxy($C_{1-4}$)alkyl (especially optionally substituted pyridyloxy- or pyrimidinyloxy($C_{1-4}$)alkyl, acyloxy, including $C_{1-4}$ alkanoyloxy (especially acetyloxy) and benzoyloxy, cyano, isocyano, thiocyanato, isothiocyanato, nitro, —NR'R", —NHCOR', —NHCONR'R", —CONR'R", —COOR', —OSO$_2$R', —SO$_2$R', —COR', —CR'=NR" or —N=CR'R" in which R' and R" are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy.

Substituents which may be present in the aryl or heteroaryl rings of any of the foregoing substituents include one or more of the following: halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$)alkoxy, $C_{1-4}$ alkylthio, hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, alkanoyloxy, benzoyloxy, cyano, isocyano, thiocyanato, isothiocyanato, nitro, —NR'R", —NHCOR', —NHCONR'R", —CONR'R", —COOR', —SO$_2$R', —OSO$_2$R', —COR', —CR'=NR" or —N=CR'R" in which R' and R" have the meanings given above.

In one aspect the invention includes a compound of formula (I) wherein A is hydrogen, halo, hydroxy, methyl, methoxy, trifluoromethyl, trifluoromethoxy, $C_{1-2}$ alkylcarbonyl, $C_{1-2}$ alkoxycarbonyl, phenoxy, nitro or cyano; $R^1$ is $C_{1-4}$ alkyl, halo($C_{1-4}$)alkyl, $C_{1-4}$ alkoxy, halo($C_{1-4}$)alkoxy, $C_{1-4}$ alkylcarbonyl, $C_{1-4}$ alkoxycarbonyl, cyano, phenyl($C_{1-4}$)alkyl, phenyl, a 5- or 6-membered aromatic heterocycle containing one or more O, N or S atoms and optionally fused to a benzene ring, the aromatic or heteroaromatic moieties of any of the foregoing being optionally substituted with one or more of halo, hydroxy, $C_{1-4}$ alkyl, halo($C_{1-4}$)alkyl, $C_{1-4}$ alkoxy, halo($C_{1-4}$)alkoxy, $C_{1-4}$ alkylcarbonyl, $C_{1-4}$ alkoxycarbonyl, nitro, cyano, phenyl, phenoxy, benzyl or benzyloxy; and $R^2$ is hydrogen, halo, $C_{1-4}$ alkyl, halo($C_{1-4}$)alkyl, $C_{1-4}$ alkylcarbonyl, $C_{1-4}$ alkoxycarbonyl, cyano or phenyl; or $R^1$ and $R^2$ join together to form a $C_{5-10}$ carbocyclic ring system.

In another aspect the invention includes a compound of formula (I) wherein A is hydrogen or halo; $R^1$ is $C_{1-4}$ alkyl, benzyl, $C_{1-4}$ alkylcarbonyl, $C_{1-4}$ alkoxycarbonyl, cyano, phenyl, thienyl, triazolyl, thiazolyl, pyridyl, pyrimidinyl, pyrazinyl, pyridazinyl, triazinyl, quinolinyl or quinoxalinyl, the aromatic or heteroaromatic moieties of any of the foregoing being optionally substituted with one or more of halo, $C_{1-4}$ alkyl, trifluoromethyl, $C_{1-4}$ alkoxy, trifluoromethoxy, nitro, cyano, phenyl or benzyloxy; and $R^2$ is hydrogen, $C_{1-4}$ alkyl, $C_{1-4}$ alkylcarbonyl, $C_{1-4}$ alkoxycarbonyl, cyano or phenyl; or $R^1$ and $R^2$ join together to form a cyclopentyl or cyclohexyl ring to which is optionally fused a benzene ring; and $R^5$ and $R^6$ are independently hydrogen or $C_{1-4}$ alkyl.

In yet another aspect the invention includes a compound of formula (I) wherein A is hydrogen; $R^1$ is phenyl, thienyl, furyl, pyrrolyl, imidazolyl, triazolyl, thiazolyl, oxazolyl, isoxazolyl, pyrazolyl, pyridyl, pyrimidinyl, pyrazinyl, pyridazinyl, triazinyl, quinolinyl, quinoxalinyl, benzthiazolyl, benzoxazolyl, benzothienyl or benzofuryl, the aromatic or heteroaromatic moieties of any of the foregoing being optionally substituted with one or more of halo, $C_{1-6}$ alkyl, halo($C_{1-4}$)alkyl (especially trifluoromethyl and trifluoroethyl), $C_{1-6}$ alkoxy, cyano($C_{1-4}$)alkoxy, halo($C_{1-4}$)alkoxy (especially trifluoromethoxy), $C_{1-4}$ alkoxy($C_{1-4}$)alkyl, $C_{1-4}$alkoxy($C_{1-4}$)alkoxy, $C_{1-4}$alkoxy($C_{1-4}$)alkoxy($C_{1-4}$)alkoxy, $C_{1-6}$ alkylthio, $C_{2-6}$ alkenyl, $C_{2-6}$ alkenyloxy, $C_{2-6}$ alkynyl, $C_{2-6}$ alkynyloxy, nitro, cyano, phenyl, phenoxy, benzyloxy, CO$_2$R', CONR'R", CSNR'R", NR'R", S(O)$_n$R', NHCONR'R", in which R' and R" are independently H or $C_{1-4}$ alkyl and n is 0, 1 or 2; $R^2$ is methyl; $R^5$ is hydrogen and $R^6$ is methyl; or, where appropriate, the N-oxide thereof.

This invention is illustrated by the compounds listed in Tables I, II and III which follow. Throughout the Tables the O-methyl oxyiminoacetamide group has the (E)-configuration.

Table I consists of 350 compounds of formula (I.1) in which the values of $R^1$, $R^2$ and A are given in the Table.

TABLE I

| Compound No. | $R^1$ | $R^2$ | A |
|---|---|---|---|
| 1 | 2-CH$_3$O—C$_6$H$_4$ | H | H |
| 2 | 3-CH$_3$O—C$_6$H$_4$ | H | H |
| 3 | 4-CH$_3$O—C$_6$H$_4$ | H | H |
| 4 | 2-CH$_3$—C$_6$H$_4$ | H | H |
| 5 | 3-CH$_3$—C$_6$H$_4$ | H | H |
| 6 | 4-CH$_3$—C$_6$H$_4$ | H | H |
| 7 | 2-F—C$_6$H$_4$ | H | H |
| 8 | 3-F—C$_6$H$_4$ | H | H |
| 9 | 4-F—C$_6$H$_4$ | H | H |
| 10 | 2-Cl—C$_6$H$_4$ | H | H |
| 11 | 3-Cl—C$_6$H$_4$ | H | H |
| 12 | 4-Cl—C$_6$H$_4$ | H | H |
| 13 | 2-Br—C$_6$H$_4$ | H | H |
| 14 | 3-Br—C$_6$H$_4$ | H | H |
| 15 | 4-Br—C$_6$H$_4$ | H | H |
| 16 | 2-NO$_2$—C$_6$H$_4$ | H | H |

TABLE I-continued

| Compound No. | R¹ | R² | A |
| --- | --- | --- | --- |
| 17 | 3-NO$_2$—C$_6$H$_4$ | H | H |
| 18 | 4-NO$_2$—C$_6$H$_4$ | H | H |
| 19 | 2-CF$_3$—C$_6$H$_4$ | H | H |
| 20 | 3-CF$_3$—C$_6$H$_4$ | H | H |
| 21 | 4-CF$_3$—C$_6$H$_4$ | H | H |
| 22 | C$_6$H$_5$ | H | H |
| 23 | C$_6$H$_5$ | CH$_3$ | H |
| 24 | C$_6$H$_5$ | C$_6$H$_5$ | H |
| 25 | 2-C$_6$H$_5$—C$_6$H$_4$ | H | H |
| 26 | 3-C$_6$H$_5$—C$_6$H$_4$ | H | H |
| 27 | 4-C$_6$H$_5$—C$_6$H$_4$ | H | H |
| 28 | 2-(C$_6$H$_5$CH$_2$O)—C$_6$H$_4$ | H | H |
| 29 | 3-(C$_6$H$_5$CH$_2$O)—C$_6$H$_4$ | H | H |
| 30 | 4-(C$_6$H$_5$CH$_2$O)—C$_6$H$_4$ | H | H |
| 31 | 2-cyano-C$_6$H$_4$ | H | H |
| 32 | 3-cyano-C$_6$H$_4$ | H | H |
| 33 | 4-cyano-C$_6$H$_4$ | H | H |
| 34 | 2-CF$_3$O—C$_6$H$_4$ | H | H |
| 35 | 3-CF$_3$O—C$_6$H$_4$ | H | H |
| 36 | 4-CF$_3$O—C$_6$H$_4$ | H | H |
| 37 | pyrid-2-yl | H | H |
| 38 | pyrid-3-yl | H | H |
| 39 | pyrid-4-yl | H | H |
| 40 | pyrid-2-yl | CH$_3$ | H |
| 41 | pyrid-2-yl | cyano | H |
| 42 | pyrid-2-yl | CO$_2$C$_2$H$_5$ | H |
| 43 | pyrid-2-yl | CO$_2$CH$_3$ | H |
| 44 | pyrimidin-2-yl | H | H |
| 45 | pyrimidin-4-yl | H | H |
| 46 | thien-2-yl | H | H |
| 47 | thien-2-yl | CH$_3$ | H |
| 48 | 5-Cl-thien-2-yl | H | H |
| 49 | CO$_2$C$_2$H$_5$ | CO$_2$C$_2$H$_5$ | H |
| 50 | CO$_2$CH$_3$ | CO$_2$CH$_3$ | H |
| 51 | COCH$_3$ | COCH$_3$ | H |
| 52 | cyano | cyano | H |
| 53 | ∅ | ∅ | H |
| 54 | ∅ | ∅ | H |
| 55 | ∅ | ∅ | H |
| 56 | tert-C$_4$H$_9$ | H | H |
| 57 | C$_6$H$_5$CH$_2$ | H | H |
| 58 | 2,4-di-Cl—C$_6$H$_3$ | H | H |
| 59 | 2,4-di-F—C$_6$H$_3$ | H | H |
| 60 | 3,5-di-CH$_3$—C$_6$H$_3$ | H | H |
| 61 | 3,5-di-CH$_3$O—C$_6$H$_3$ | H | H |
| 62 | pyrazin-2-yl | CH$_3$ | H |
| 63 | 6-CH$_3$-pyrid-3-yl | CH$_3$ | H |
| 64 | pyrid-2-yl | C$_2$H$_5$ | H |
| 65 | pyrid-3-yl | CH$_3$ | H |
| 66 | pyrimidin-5-yl | iso-C$_3$H$_7$ | H |
| 67 | iso-C$_3$H$_7$ | pyrimidin-5-yl | H |
| 68 | pyrid-4-yl | CH$_3$ | H |
| 69 | 6-Cl-pyrid-2-yl | CH$_3$ | H |
| 70 | 5-Cl-pyrid-2-yl | CH$_3$ | H |
| 71 | 4-Cl-pyrid-2-yl | CH$_3$ | H |
| 72 | 3-Cl-pyrid-2-yl | CH$_3$ | H |
| 73 | 6-cyano-pyrid-2-yl | CH$_3$ | H |
| 74 | 5-cyano-pyrid-2-yl | CH$_3$ | H |
| 75 | 4-cyano-pyrid-2-yl | CH$_3$ | H |
| 76 | 3-cyano-pyrid-2-yl | CH$_3$ | H |
| 77 | 6-Br-pyrid-2-yl | CH$_3$ | H |
| 78 | 5-Br-pyrid-2-yl | CH$_3$ | H |
| 79 | 4-Br-pyrid-2-yl | CH$_3$ | H |
| 80 | 3-Br-pyrid-2-yl | CH$_3$ | H |
| 81 | 6-CH$_3$-pyrid-2-yl | CH$_3$ | H |
| 82 | 5-CH$_3$-pyrid-2-yl | CH$_3$ | H |
| 83 | 4-CH$_3$-pyrid-2-yl | CH$_3$ | H |
| 84 | 3-CH$_3$-pyrid-2-yl | CH$_3$ | H |
| 85 | 6-F-pyrid-2-yl | CH$_3$ | H |
| 86 | 5-F-pyrid-2-yl | CH$_3$ | H |
| 87 | 4-F-pyrid-2-yl | CH$_3$ | H |
| 88 | 3-F-pyrid-2-yl | CH$_3$ | H |
| 89 | 3-CH$_3$-pyrazin-2-yl | CH$_3$ | H |
| 90 | 3-C$_2$H$_5$-pyrazin-2-yl | CH$_3$ | H |
| 91 | 3-Cl-pyrazin-2-yl | CH$_3$ | H |
| 92 | 3-OCH$_3$-pyrazin-2-yl | CH$_3$ | H |
| 93 | 5-CO$_2$CH$_3$-pyrazin-2-yl | CH$_3$ | H |
| 94 | 5-CO$_2$C$_2$H$_5$-pyrazin-2-yl | CH$_3$ | H |
| 95 | 3-cyano-pyrazin-2-yl | CH$_3$ | H |
| 96 | pyrimidin-4-yl | CH$_3$ | H |

TABLE I-continued

| Compound No. | R¹ | R² | A |
|---|---|---|---|
| 97 | 2-Cl-pyrimidin-4-yl | $CH_3$ | H |
| 98 | 2-$OCH_3$-pyrimidin-4-yl | $CH_3$ | H |
| 99 | 2-$CH_3$-pyrimidin-4-yl | $CH_3$ | H |
| 100 | 2-cyano-pyrimidin-4-yl | $CH_3$ | H |
| 101 | thiazol-2-yl | $CH_3$ | H |
| 102 | thien-3-yl | $CH_3$ | H |
| 103 | 5-Cl-thien-2-yl | $CH_3$ | H |
| 104 | 5-$CH_3$-thien-2-yl | $CH_3$ | H |
| 105 | 5-Br-thien-2-yl | $CH_3$ | H |
| 106 | 5-cyano-thien-2-yl | $CH_3$ | H |
| 107 | 3-$CH_3$-thien-2-yl | $CH_3$ | H |
| 108 | 2-$OCH_3$—$C_6H_4$ | $CH_3$ | H |
| 109 | 3-$OCH_3$—$C_6H_4$ | $CH_3$ | H |
| 110 | 4-$OCH_3$—$C_6H_4$ | $CH_3$ | H |
| 111 | 2-$CH_3$—$C_6H_4$ | $CH_3$ | H |
| 112 | 3-$CH_3$—$C_6H_4$ | $CH_3$ | H |
| 113 | 4-$CH_3$—$C_6H_4$ | $CH_3$ | H |
| 114 | 2-F—$C_6H_4$ | $CH_3$ | H |
| 115 | 3-F—$C_6H_4$ | $CH_3$ | H |
| 116 | 4-F—$C_6H_4$ | $CH_3$ | H |
| 117 | 2-Cl—$C_6H_4$ | $CH_3$ | H |
| 118 | 3-Cl—$C_6H_4$ | $CH_3$ | H |
| 119 | 4-Cl—$C_6H_4$ | $CH_3$ | H |
| 120 | 2-Br—$C_6H_4$ | $CH_3$ | H |
| 121 | 3-Br—$C_6H_4$ | $CH_3$ | H |
| 122 | 4-Br—$C_6H_4$ | $CH_3$ | H |
| 123 | 2-$NO_2$—$C_6H_4$ | $CH_3$ | H |
| 124 | 3-$NO_2$—$C_6H_4$ | $CH_3$ | H |
| 125 | 4-$NO_2$—$C_6H_4$ | $CH_3$ | H |
| 126 | 2-$CF_3$—$C_6H_4$ | $CH_3$ | H |
| *127 | 3-$CF_3$—$C_6H_4$ | $CH_3$ | H |
| 128 | 4-$CF_3$—$C_6H_4$ | $CH_3$ | H |
| 129 | 2-cyano-$C_6H_4$ | $CH_3$ | H |
| 130 | 3-cyano-$C_6H_4$ | $CH_3$ | H |
| 131 | 4-cyano-$C_6H_4$ | $CH_3$ | H |
| 132 | 3,4,5-$(OCH_3)_3$—$C_6H_2$ | $CH_3$ | H |
| 133 | 3,5-di-F-pyrid-2-yl | $CH_3$ | H |
| 134 | 3,4,5,6-$F_4$-pyrid-2-yl | $CH_3$ | H |
| 135 | 2,6-di-Cl-pyrid-3-yl | $CH_3$ | H |
| 136 | pyridazin-3-yl | $CH_3$ | H |
| 137 | pyridazin-4-yl | $CH_3$ | H |
| 138 | 6-$CH_3$-pyridazin-3-yl | $CH_3$ | H |
| 139 | 4-cyano-quinolin-2-yl | $CH_3$ | H |
| 140 | quinoxalin-2-yl | $CH_3$ | H |
| 141 | $C_6H_5$ | $CH_3$ | 6-F |
| 142 | $C_6H_5$ | $CH_3$ | 6-Cl |
| 143 | 6-$CH_3$-pyrimidin-4-yl | $CH_3$ | H |
| 144 | 4-$CH_3$-pyrimidin-5-yl | $CH_3$ | H |
| 145 | 4-$CH_3$-pyrimidin-2-yl | $CH_3$ | H |
| 146 | 4,6-di-$CH_3$-pyrimidin-2-yl | $CH_3$ | H |
| 147 | 2,6-di-$CH_3$-pyrimidin-4-yl | $CH_3$ | H |
| 148 | 2,4-di-$CH_3$-pyrimidin-5-yl | $CH_3$ | H |
| 149 | 6-Cl-pyrimidin-4-yl | $CH_3$ | H |
| 150 | 6-$OCH_3$-pyrimidin-4-yl | $CH_3$ | H |
| 151 | 4,6-di-$OCH_3$-pyrimidin-2-yl | $CH_3$ | H |
| 152 | ∅ | ∅ | H |
| 153 | ∅ | ∅ | H |
| 154 | _N_-oxide-pyrid-2-yl | $CH_3$ | H |
| 155 | 5-$C_2H_5$-pyrid-2-yl | $CH_3$ | H |
| 156 | $CH_3CO$ | $CH_3$ | H |
| 157 | $C_6H_5CO$ | $CH_3$ | H |
| 158 | _N_—$CH_3$-pyrrol-2-yl | $CH_3$ | H |
| 159 | 4-Cl-quinolin-2-yl | $CH_3$ | H |
| 160 | 2,4-di-Cl-$C_6H_3$ | 1,2,4-triazol-1-yl-$CH_2$ | H |
| 161 | 2,4-di-Cl—$C_6H_3$ | pyrid-3-yl-$CH_2$ | H |
| 162 | 2,4-di-$CH_3$-thiazol-5-yl | $CH_3$ | H |
| 163 | furan-2-yl | $CH_3$ | H |
| 164 | 2,4-di-$CH_3$-furan-3-yl | $CH_3$ | H |
| 165 | pyrid-2-yl | pyrid-2-yl | H |
| 166 | 6-$C_6H_5$-pyrimidin-4-yl | $CH_3$ | H |
| 167 | 4-cyano-pyrid-3-yl | $CH_3$ | H |
| 168 | 1,2,4-triazin-5-yl | $CH_3$ | H |
| 169 | 3-$CH_3$-1,2,4-triazin-5-yl | $CH_3$ | H |
| 170 | 3-$C_6H_5$-1,2,4-triazin-5-yl | $CH_3$ | H |
| 171 | 3-$SCH_3$-1,2,4-triazin-5-yl | $CH_3$ | H |
| 172 | 3-$OCH_3$-1,2,4-triazin-5-yl | $CH_3$ | H |
| 173 | 5-$CONH_2$-pyrazin-2-yl | $CH_3$ | H |
| 174 | 5-cyano-pyrazin-2-yl | $CH_3$ | H |
| 175 | 5,6-di-$CH_3$-pyrazin-2-yl | $CH_3$ | H |

TABLE I-continued

| Compound No. | R¹ | R² | A |
|---|---|---|---|
| 176 | 3,5-di-$CH_3$-pyrazin-2-yl | $CH_3$ | H |
| 177 | 3,6-di-$CH_3$-pyrazin-2-yl | $CH_3$ | H |
| 178 | 5-$CH_3$-pyrazin-2-yl | $CH_3$ | H |
| 179 | 6-$CH_3$-pyrazin-2-yl | $CH_3$ | H |
| 180 | 5-Cl-pyrazin-2-yl | $CH_3$ | H |
| 181 | 6-Cl-pyrazin-2-yl | $CH_3$ | H |
| 182 | 5,6-dicyano-pyrazin-2-yl | $CH_3$ | H |
| 183 | 4-$SO_2CH_3$—$C_6H_4$ | $CH_3$ | H |
| 184 | 4-$NH_2$—$C_6H_4$ | $CH_3$ | H |
| 185 | 2,4-di-Cl—$C_6H_3$ | $CH_3$ | H |
| 186 | 2,4-di-$CH_3$—$C_6H_3$ | $CH_3$ | H |
| 187 | 4-$NHCONH_2$—$C_6H_4$ | $CH_3$ | H |
| 188 | $C_6H_5$ | cyclopropyl | H |
| 189 | $C_6H_5$ | Cl | H |
| 190 | 4-$C_2H_5O$—$C_6H_4$ | $CF_3$ | H |
| 191 | $C_6H_5$ | $SCH_3$ | H |
| 192 | $C_6H_5$ | F | H |
| 193 | $C_6H_5$ | $OC_2H_5$ | H |
| 194 | $C(CH_3)_3$ | $CH_3$ | H |
| 195 | cyclohexyl-$CH_2$ | $CH_3$ | H |
| 196 | $C_6H_5$—$CH_2$ | $CH_3$ | H |
| 197 | pyrazin-2-yl-$CH_2$ | $CH_3$ | H |
| 198 | (E)-$C_6H_5$—CH=CH | $CH_3$ | H |
| 199 | $C_6H_5OCH_2$ | $CH_3$ | H |
| 200 | $C_6H_5$ | $CH_2Cl$ | H |
| 201 | benzthiazol-2-yl | $CH_3$ | H |
| 202 | benzoxazol-2-yl | $CH_3$ | H |
| 203 | pyrazin-2-yl | $C_2H_5$ | H |
| 204 | 5-$OCH_3$-pyrazin-2-yl | $CH_3$ | H |
| 205 | 6-$OCH_3$-pyrazin-2-yl | $CH_3$ | H |
| 206 | 6-cyano-pyrazin-2-yl | $CH_3$ | H |
| 207 | 5-cyano-pyrid-3-yl | $CH_3$ | H |
| 208 | 6-cyano-pyrid-3-yl | $CH_3$ | H |
| 209 | 3-cyano-pyrid-4-yl | $CH_3$ | H |
| 210 | 2-cyano-pyrid-4-yl | $CH_3$ | H |
| 211 | pyrimidin-5-yl | $CH_3$ | H |
| 212 | 2-$CH_3$-pyrimidin-5-yl | $CH_3$ | H |
| 213 | 3-$OCH_3$-isoxazol-5-yl | $CH_3$ | H |
| 214 | 3-Br-isoxazol-5-yl | $CH_3$ | H |
| 215 | 5-$NO_2$-thiazol-2-yl | $CH_3$ | H |
| 216 | 5-$CH_3$-thiazol-2-yl | $CH_3$ | H |
| 217 | 4-$CH_3$-thiazol-5-yl | $CH_3$ | H |
| 218 | 2-Cl,4-$CH_3$-thiazol-5-yl | $CH_3$ | H |
| 219 | 3,5-di-$OCH_3$-1,2,4-triazin-6-yl | $CH_3$ | H |
| 220 | 3,6-di-$CH_3$-pyridazin-4-yl | $CH_3$ | H |
| 221 | 2-($C_6H_5O$)—$C_6H_4$ | $CH_3$ | H |
| 222 | 3-($C_6H_5O$)—$C_6H_4$ | $CH_3$ | H |
| 223 | 4-($C_6H_5O$)—$C_6H_4$ | $CH_3$ | H |
| 224 | 1,2,4-triazol-1-yl-$CH_2$ | $CH_3$ | H |
| 225 | $C_6H_5$ | $OCH_3$ | H |
| 226 | $OCH_3$ | $C_6H_5$ | H |
| 227 | $C_6H_5$ | $CH_3S(O)$ | H |
| 228 | $C_6H_5$ | $CH_3S(O)_2$ | H |
| 229 | $C_6H_5$ | $N(CH_3)_2$ | H |
| 230 | $C_6H_5O$ | $CH_3$ | H |
| 231 | $C_6H_5$ | Br | H |
| 232 | $C_6H_5$ | I | H |
| 233 | $C_6H_5$ | $(CH_3)_2CHS$ | H |
| 234 | Pyrimidin-2-yl | $CH_3O$ | H |
| 235 | Pyrazin-2-yl | Cl | H |
| 236 | 3-$OC_2H_5$-pyrazin-2-yl | $CH_3$ | H |
| 237 | pyrid-2-yl | $SCH_3$ | H |
| 238 | pyrid-2-yl | $SO_2CH_3$ | H |
| 239 | Pyrid-2-yl | $SOCH_3$ | H |
| 240 | 3,5-di-$CH_3$-oxazol-4-yl | $CH_3$ | H |
| 241 | pyrid-2-yl | $OCH_3$ | H |
| 242 | pyrid-2-yl | $SC_2H_5$ | H |
| 243 | pyrid-2-yl | $OC_6H_5$ | H |
| 244 | pyrid-2-yl | $OCH_2$—$C_6H_5$ | H |
| 245 | 6-$OC_2H_5$-pyrimidin-4-yl | $CH_3$ | H |
| 246 | pyrid-2-yl | $NH_2$ | H |
| 247 | $SCH_3$ | pyrid-2-yl | H |
| 248 | 2,4-di-F—$C_6H_3$ | $CH_3$ | H |
| 249 | 2,4-di-$OCH_3$—$C_6H_3$ | $CH_3$ | H |
| 250 | 5-$CH_3$-pyrimidin-2-yl | $CH_3$ | H |
| 251 | $SO_2CH_3$ | pyrid-2-yl | H |
| 252 | pyrid-3-yl | $SCH_3$ | H |
| 253 | pyrid-3-yl | $OCH_3$ | H |
| 254 | 6-$CF_3$-pyrid-2-yl | $CH_3$ | H |

TABLE I-continued

| Compound No. | R¹ | R² | A |
|---|---|---|---|
| 255 | 3-CF₃-4-F—C₆H₃ | CH₃ | H |
| 256 | 6-CF₃-pyrimidin-4-yl | CH₃ | H |
| 257 | 3,5-di-F—C₆H₃ | CH₃ | H |
| 258 | 2-CH₃CH₂S-pyrimidin-4-yl | CH₃ | H |
| 259 | 2-CF₃-pyrimidin-4-yl | CH₃ | H |
| 260 | 4-CF₃-pyrid-2-yl | CH₃ | H |
| 261 | 2-phenyl-thiazol-4-yl | CH₃ | H |
| 262 | 3-NH₂C(O)—C₆H₄ | CH₃ | H |
| 263 | 4-CF₃-pyrimidin-2-yl | CH₃ | H |
| 264 | 3,5-di-CF₃C₆H₃ | CH₃ | H |
| 265 | 2-(2-CN—C₆H₄—O—)-pyrimidin-4-yl | CH₃ | H |
| 266 | 3-n-C₃H₇O—C₆H₄ | CH₃ | H |
| 267 | 2-CH(CH₃)₂-O-pyrimidin-4-yl | CH₃ | H |
| 268 | 6-CF₃-pyrazin-2-yl | CH₃ | H |
| 269 | 4-C₂H₅O-pyrimidin-2-yl | CH₃ | H |
| 270 | 6-C₂F₅-din-4-yl | CH₃ | H |
| 271 | 3-CF₃O—C₆H₄ | CH₃ | H |
| 272 | 4-CH₃O-pyrid-2-yl | CH₃ | H |
| 273 | 2-propargyloxy-pyrimidin-4-yl | CH₃ | H |
| 274 | 2-C₂H₅O-pyrimidin-4-yl | CH₃ | H |
| 275 | 2-allyloxy-pyrimidin-4-yl | CH₃ | H |
| 276 | 3-CH₃O-pyridazin-6-yl | CH₃ | H |
| 277 | 3-C₂H₅O-pyridazin-6-yl | CH₃ | H |
| 278 | 3-allyloxy-C₆H₄ | CH₃ | H |
| 279 | 4-CH₃S-pyrimidin-2-yl | CH₃ | H |
| 280 | 4-CH₃O-pyrimidin-2-yl | CH₃ | H |
| 281 | 3-CF₃—C₆H₄ | SCH₃ | H |
| 282 | 3-CF₃—C₆H₄ | CF₃ | H |
| 283 | 3-CF₃—C₆H₄ | C₂H₅ | H |
| 284 | 3-CF₃—C₆H₄ | NH₂ | H |
| 285 | 3-CF₃—C₆H₄ | imidazolyl | H |
| 286 | 3-CF₃—C₆H₄ | N(CH₃)₂ | H |
| 287 | 3-CF₃—C₆H₄ | NHCH₃ | H |
| 288 | PO(OC₂H₅)₂ | CH₃ | H |
| 289 | PO(OC₂H₅)₂ | C₆H₅ | H |
| 290 | 4-CH₃O-6-(CO₂CH₃)-pyrimidin-2-yl | CH₃ | H |
| 291 | pyrrol-2-yl | CH₃ | H |
| 292 | CH₃ | pyrrol-2-yl | H |
| 293 | 5-CF₃-pyrid-3-yl | CH₃ | H |
| 294 | 3-(pyrimidinyloxy)-C₆H₄ | CH₃ | H |
| 295 | 3-propargyloxy-C₆H₄ | CH₃ | H |
| 296 | CH₃ | H | H |
| 297 | 5-(2,4-difluorophenyl)-furan-2-yl | CH₃ | H |
| 298 | CH₃ | 5-(2,4-difluorophenyl)-furan-2-yl | H |
| 299 | C₂H₅O | CH₃ | H |
| 300 | 4-tert-butyl-C₆H₄ | CH₃ | H |
| 301 | 4-propargyloxy-pyrimidin-2-yl | CH₃ | H |
| 302 | 2-C₂H₅O—C₆H₄ | CH₃ | H |
| 303 | 4-C₂H₅—C₆H₄ | CH₃ | H |
| 304 | 3-C₂H₅O—C₆H₄ | CH₃ | H |
| 305 | CH₃S | CH₃ | H |
| 306 | CH₃SO₂ | CH₃ | H |
| 307 | ∅ | ∅ | H |
| 308 | 4-n-C₃H₇O-pyrimidin-2-yl | CH₃ | H |
| 309 | 3-n-hexyloxy-C₆H₄ | CH₃ | H |
| 310 | 4-n-butyloxy-pyrimidin-2-yl | CH₃ | H |
| 311 | benzothiophen-3-yl | CH₃ | H |
| 312 | 3-[(CH₃)₂C=CHCH₂]—C₆H₄ | CH₃ | H |
| 313 | 2,4-di-CH₃O-pyrimidin-6-yl | CH₃ | H |
| 314 | 3-CF₃—C₆H₄ | 1,2,4-triazol-1-yl | H |
| 315 | 3-CH₃S-pyrazin-2-yl | CH₃ | H |
| 316 | 3-N(CH₃)₂—C₆H₄ | CH₃ | H |
| 317 | 3-CF₃—C₆H₄ | Cl | H |
| 318 | ∅ | ∅ | H |
| 319 | benzofuran-2-yl | CH₃ | H |
| 320 | 2-CH₃S(O)-pyrimidin-4-yl | CH₃ | H |
| 321 | 3-NH₂C(S)—C₆H₄ | CH₃ | H |
| 322 | 4-NH₂C(S)-pyrid-2-yl | CH₃ | H |
| 323 | 3-(CH₃OCH₂CH₂OCH₂O)—C₆H₄ | CH₃ | H |
| 324 | 3-(cyanomethoxy)-C₆H₄ | CH₃ | H |
| 325 | ∅ | ∅ | H |
| 326 | 3-(F₂HCO)—C₆H₄ | CH₃ | H |
| 327 | 6-C₂H₅O-pyrazin-2-yl | CH₃ | H |
| 328 | 4-CH₃-6-OCH₃-pyrimidin-2-yl | CH₃ | H |
| 329 | 4-CH₃-thien-2-yl | CH₃ | H |
| 330 | 2,4-di-CH₃-thiazol-5-yl | CH₃ | H |
| 331 | 4-CF₃-6-CH₃-pyrimidin-2-yl | CH₃ | H |
| 332 | 5-Br-pyrid-3-yl | CH₃ | H |

TABLE I-continued

| Compound No. | R¹ | R² | A |
|---|---|---|---|
| 333 | 5-CONHCH₃-pyrazin-2-yl | CH₃ | H |
| 334 | 4,6-di-OC₂H₅-pyrimidin-2-yl | CH₃ | H |
| +335 | 5-CH₃-furan-2-yl | CH₃ | H |
| +335A | 5-CH₃-furan-2-yl | CH₃ | H |
| 336 | 2-SCH₃-pyrimidin-4-yl | CH₃ | H |
| 337 | 4-iso-C₃H₇O-pyrimidin-2-yl | CH₃ | H |
| 338 | N-CH₃-3-CH₃-5-OC₆H₅-pyrazol-4-yl | H | H |
| 339 | 3-CH₃-benzothiophen-2-yl | CH₃ | H |
| 340 | 4-OCH₂CF₃-pyrimidin-2-yl | CH₃ | H |
| 341 | 2-N(CH₃)₂-pyrimidin-4-yl | CH₃ | H |
| 342 | 5-NO₂-pyrid-2-yl | CH₃ | H |
| 343 | 2-tert-C₄H₉-pyrimidin-5-yl | CH₃ | H |
| 344 | 5-NO₂-benzofuran-2-yl | CH₃ | H |
| 345 | 4-O(CH₂)₂OCH₃-pyrid-2-yl | CH₃ | H |
| 346 | 3,4-di-Cl—C₆H₃ | CH₃ | H |
| 347 | 6-OC₂H₅-pyrid-2-yl | CH₃ | H |
| 348 | 4-CF₃-6-OCH₂CF₃-pyrid-2-yl | CH₃ | H |
| 349 | 4-CF₃-6-OC₂H₅-pyrid-2-yl | CH₃ | H |
| 350 | 5-CF₃-pyrid-2-yl | CH₃ | H |

Key
*For a preparation of this compound, see Example 1.
+Compound 335 is one isomer and compound 335A is a 2:1 mixture of two isomers.
∅ Groups R1 and R2 join to form a ring as shown under 'Chemical Formulae' later.

Table II consists of 350 compounds of the formula (I.2). The values of R¹, R² and A of each compound correspond to the values given for the compound of the same number in Table I. The only difference between the compounds of Table I and Table II is that the compounds of Table I have a single N-methyl substituent on the acetamide group, whereas the compounds of Table II have two N-methyl substituents on the acetamide group.

Table III consists of 350 compounds of the formula (I.3). The values of R¹, R² and A of each compound correspond to the values given for the compound of the same number in Table I. The only difference between the compounds of Table I and Table III is that the compounds of Table I have an N-methyl substituent on the acetamide group, whereas the compounds of Table III have no N-substituents on the acetamide group.

TABLE IV

Table IV gives melting points or selected proton NMR data obtained at MHz for certain compounds described in Table I and for compound No. 346 in Table III. Chemical shifts are measured at 20° C. in ppm from tetramethylsilane and deuterochloroform was used as solvent, unless otherwise stated. The following abbreviations are used:
s = singlet   m = multiplet   d = doublet
dd = double doublet   t = triplet   br = broad
ppm = parts per million

| Compound No (Table I except as shown) | Melting Point (°C.) | Proton NMR Data (δ) |
|---|---|---|
| 40 | Gum | 2.30(3H, s), 2.88(3H, d), 3.94(3H, s), 5.14(2H, s), 6.72(1H, br), 7.16–7.25(2H, m), 7.32–7.43(2H, m), 7.48–7.51(1H, m), 7.60–7.68(1H, m), 7.81–7.85(1H, d), 8.58–8.60(1H, d) ppm. |
| 47 | 77–79 | |
| 63 | 92–94 | |
| 75 | Gum | 2.28(3H, s), 2.9(3H, d), 3.95(3H, s), 5.18(2H, s), 6.8(1H,br), 7.18–7.21(1H, m), 7.31–7.51(4H, m), 8.12(1H, s), 8.70(1H, d) ppm. |
| 103 | 70–71 | |
| 109 | 53–55 | |
| 113 | 62–64 | |
| 115 | Gum | 2.18(3H, s), 2.88(3H, d), 3.95(3H, s), 5.12(2H, s), 6.73(1H, br), 6.99–7.07(1H, m), 7.17–7.22(1H, m), 7.28–7.52(6H, m) ppm. |
| 127 | Gum | 2.22(3H, s), 2.88(3H, d), 3.94(3H, s), 5.14(2H, s), 6.74(1H, br m), 7.1–7.9(8H, m) ppm |
| 158 | 76–78 | |
| 176 | Gum | 2.2(3H, s), 2.5(6H, s), 2.95(3H, d), 3.95(3H, s), 5.1(2H, s), 6.75(1H, m), 7.1–7.5(4H, m), 8.25(1H, s) ppm. |
| 188 | 105–107 | |
| 194 | 71–73 | |
| 198 | 88–90 | |
| 236 | 99–100 | |
| 260 | 120.8–122 | |
| 264 | 138–140 | |
| 269 | 121–122.5 | |
| 295 | 103–105 | |

TABLE IV-continued

Table IV gives melting points or selected proton NMR data obtained at MHz for certain compounds described in Table I and for compound No. 346 in Table III. Chemical shifts are measured at 20° C. in ppm from tetramethylsilane and deuterochloroform was used as solvent, unless otherwise stated. The following abbreviations are used:
s = singlet    m = multiplet    d = doublet
dd = double doublet    t = triplet    br = broad
ppm = parts per million

| Compound No (Table I except as shown) | Melting Point (°C.) | Proton NMR Data ($\delta$) |
|---|---|---|
| 326 | 41–43 | |
| 328 | 89–91 | |
| 329 | 73–75 | |
| 330 | 122–124 | |
| 331 | 161–163 | |
| 332 | 112–113 | |
| 333 | 140–142 | |
| 334 | 93–95 | |
| 335 | 108–109 | |
| 335A | Gum | 2:1 mixture of isomers. Major component: 2.18(3H, s), 2.32(3H, s), 2.8(3H, d), 3.92(3H, s), 5.06(2H, s), 6.07(1H, d), 6.64(1H, br), 7.03(1H, m), 7.17–7.23(1H, m), 7.33–7.45(2H, m), 7.47–7.53(1H, m) ppm. Minor component: 2.08(s), 2.34(s), 2.9(d), 3.94(s), 5.11(s), 6.02(d), 6.49(d), 6.72(br), 7.17–7.23(m), 7.33–7.45(m), 7.47–7.52(m) ppm. |
| 336 | 122–124 | |
| 337 | 97–98.5 | |
| 338 | 108–110 | |
| 339 | 136–137 | |
| 340 | 125–126 | |
| 341 | 113–116 | |
| 342 | 120–124 | |
| 343 | 87–89 | |
| 344 | 62–64 | |
| 345 | Gum | 2.29(3H, s), 2.89(3H, d), 3.46(3H, s), 3.77(2H, t), 3.96(3H, s), 4.19(2H, t), 5.16(2H, s), 6.76(1H, m), 6.81(1H, dd), 7.2–7.5(5H, m), 8.39(1H, d) ppm. |
| 346* | 114–116 | |
| 347 | 87.4–88.4 | |
| 348 | 143.5–143.9 | |
| 349 | 111.6–112.8 | |
| 35 | 118.4–118.8 | |

*Table III

The compounds of the invention can be prepared by the methods described in EP-A-0370629 and EP-A-0398692. The former reference shows how to prepare similar compounds which have a methyl $\beta$-methoxyacrylate group attached to the phenyl ring in formula I instead of an O-methyl oxyiminoacetamide group. The latter reference shows how to construct the oxyiminoacetamide group.

The invention also includes a process for preparing a compound according to claim 1 which comprises reacting a compound of the formula (II) with an amine NHR$^5$R$^6$, wherein A, R$^1$, R$^2$, R$^5$ and R$^6$ have the meanings given above, and R is H or C$_{1-4}$ alkyl.

Methyl 2-(bromomethyl)phenylglyoxylate O-methyloxime (compound A in Scheme I under "Chemical Formulae" later) provides a convenient starting material. It may be prepared, as described in EP-A-0363818, by the bromination of methyl 2-methylphenylglyoxylate O-methyloxime. The (E)-isomer of the latter compound, for use in preparing the preferred (E)-isomers of the compounds of formula (I), may be obtained from the (Z)-isomer or from a mixture of the (Z)- and (E)-isomers by isomerization under acidic conditions, for instance, as described in Example 2. Alternatively, the isomerization step may be performed as a final step on the compound of formula (I).

The compounds are active fungicides and may be used to control one or more of the following pathogens: *Pyricularia oryzae* on rice; *Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and ornamental plants; *Erysiphe graminis* (powdery mildew) on barley and wheat and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines; Helminthosporium spp., Rhynchosporium spp., Septoria spp., Pyrenophora spp., *Pseudocercosporella herpotrichoides* and *Gaeumannomyces graminis* on cereals; *Cercospora arachidicola* and *Cercosporidium personata* on peanuts and other Cercospora species on other hosts, for example, sugar beet, bananas, soya beans and rice; *Botrytis cinerea* (grey mould) on tomatoes, strawberries, vegetables, vines and other hosts; Alternaria spp. on vegetables (e.g. cucumber), oil-seed rape, apples, tomatoes and other hosts; *Venturia inaequalis* (scab) on apples; *Plasmopara viticola* on vines; other downy mildews such as *Bremia lactucae* on lettuce, Peronospora spp. on soybeans, tobacco, onions and other hosts; *Pseudoperonospora humuli* on hops and *Pseudoperonospora cubensis* on cucurbits; *Phytophthora infestans* on potatoes and tomatoes and other Phytophthora spp. on vegetables, strawberries, avocado, pepper, ornamentals, tobacco, cocoa and other hosts; *Thanatephorus cucumeris* on rice and other Rhizoctonia species on various hosts such as wheat and barley, vegetables, cotton and turf.

Some of the compounds show a broad range of activities against fungi in vitro. They may also have activity against various post-harvest diseases of fruit (e.g. *Penicillium digitatum* and *italicum* and *Trichoderma viride* on oranges, *Gloeosporium musarum* on bananas and *Botrytis cinerea* on grapes).

Further, some of the compounds may be active as seed dressings against pathogens including Fusarium spp., Septoria spp., Tilletia spp., (bunt, a seed-borne disease of wheat), Ustilago spp. and Helminthosporium spp. on cereals, *Rhizoctonia solani* on cotton and *Pyricularia oryzae* on rice.

The compounds may move acropetally/locally in plant tissue. Moreover, the compounds may be volatile enough to be active in the vapour phase against fungi on the plant.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides fungicidal compositions comprising a compound as hereinbefore defined and an acceptable carrier or diluent therefor.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatments.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment.

These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or N,N-dimethylformamide). The compositions may also be in the form of wettable powders or water dispersable granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10-85%, for example 25-60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which possess plant growth regulating, herbicidal or insecticidal activity.

A fungicidal compound which may be present in the composition of the invention may be one which is capable of combating ear diseases of cereals (e.g. wheat) such as Septoria, Gibberella and Helminthosporium spp., seed and soil-borne diseases and downy and powdery mildews on grapes and powdery mildew and scab on apple, etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are (RS)-1-aminopropylphosphonic acid, (RS)-4-(4-chlorophenyl)-2-phenyl-2-(1H-1,2,4-triazol-1-ylmethyl)butyronitrile, (Z)-N-but-2-enyloxymethyl-2-chloro-2',6'-diethylacetanilide, 1-(2-cyano-2-methoxyiminoacetyl)-3-ethyl urea, 3-(2,4-dichlorophenyl)-2-(1H-1,2,4-triazol-1-yl)quinazolin-4(3H)-one, 4-bromo-2-cyano-N,N-dimethyl-6-trifluoromethylbenzimidazole-1-sulphonamide, 5-ethyl-5,8-dihydro-8-oxo(1,3)-dioxol-(4,5-g)quinoline-7-carboxylic acid, α-[N-(3-chloro-2,6-xylyl)-2-methoxyacetamido]-γ-butyrolactone, aldimorph, anilazine, benalaxyl, benomyl, biloxazol, binapacryl, bitertanol, blasticidin S, bromuconazole, bupirimate, buthiobate, captafol, captan, carbendazim, carboxin, chlorbenzthiazone, chloroneb, chlorothalonil, chlorozolinate, copper containing compounds such as copper oxychloride, copper sulphate and Bordeaux mixture, cycloheximide, cymoxanil, cyproconazole, cyprofuram, di-2-pyridyl disulphide 1,1'-dioxide, dichlofluanid, dichlone, diclobutrazol, diclomezine, dicloran, difenoconazole, dimethamorph, dimethirimol, diniconazole, dinocap, ditalimfos, dithianon, dodemorph, dodine, edifenphos, etaconazole, ethirimol, ethyl (Z)-N-benzyl-N-([methyl(methylthioethylideneamino-oxycarbonyl)amino]thio)-β-alaninate, etridiazole, fenapanil, fenarimol, fenfuram, fenpiclonil, fenpropidin, fenpropimorph, fentin acetate, fentin hydroxide, flutolanil, flutriafol, flusilazole, folpet, fosetyl-aluminium, fuberidazole, furalaxyl, furconazole-cis, guazatine, hexaconazole, hydroxyisoxazole, imazalil, imibenconazole, iprobenfos, iprodione, isoprothiolane, kasugamycin, mancozeb, maneb, mepanipyrim, mepronil, metalaxyl, methfuroxam, metsulfovax, myclobutanil, neoasozin, nickel dimethyldithiocarbamate, nitrothal-isopropyl, nuarimol, ofurace, organomercury compounds, oxadixyl, oxycarboxin, perfurazoate, penconazole, pencycuron, phenazin oxide, phthalide, polyoxin D, polyram, probenazole, prochloraz, procymidone, propamocarb, propiconazole, propineb, prothiocarb, pyrazophos, pyrifenox, pyroquilon, pyroxyfur, pyrrolnitrin, quinomethionate, quintozene, SSF-109, streptomycin, sulphur, tebuconazole, techlofthalam, tecnazene, tetraconazole, thiabendazole, thicyofen, thiophanate-methyl, thiram, tolclofos-methyl, triacetate salt of 1,1'-iminodi(octamethylene)diguanidine, triadimefon, triadimenol, triazbutyl, tricyclazole, tridemorph, triforine, validamycin A, vinclozolin, zarilamid and zineb. The compounds of general formula (I) can be mixed with soil, peat or other rooting media for the protection of plants against seed-borne, soil-borne or foliar fungal diseases.

Suitable insecticides which may be incorporated in the composition of the invention include buprofezin, carbaryl, carbofuran, carbosulfan, chlorpyrifos, cycloprothrin, demeton-s-methyl, diazinon, dimethoate, ethofenprox, fenitrothion, fenobucarb, fenthion, formothion, isoprocarb, isoxathion, monocrotophos, phenthoate, pirimicarb, propaphos and XMC.

Plant growth regulating compounds are compounds which control weeds or seedhead, formation, or selectively control the growth of less desirable plants (e.g. grasses).

Examples of suitable plant growth regulating compounds for use with the invention compounds are 3,6-dichloropicolinic acid, 1-(4-chlorophenyl)-4,6-di-methyl-2-oxo-1,2-dihydropyridine-3-carboxylic acid, methyl-3,6-dichloroanisate, abscisic acid, asulam, benzoylprop-ethyl, carbetamide, daminozide, difenzoquat, dikegulac, ethephon, fenpentezol, fluoridamid, glyphosate, glyphosine, hydroxybenzonitriles (e.g. bromoxynil), inabenfide, isopyrimol, long chain fatty alcohols and acids, maleic hydrazide, mefluidide, morphactins (e.g. chlorfluoroecol), paclobutrazol, phenoxyacetic acids (e.g. 2,4-D or MCPA), substituted benzoic acid (e.g. triiodobenzoic acid), substituted quaternary ammonium and phosphonium compounds (e.g. chloromequat, chlorphonium or mepiquatchloride), tecnazene, the auxins (e.g. indoleacetic acid, indolebutyric acid, naphthylacetic acid or naphthoxyacetic acid), the cytokinins (e.g. benzimidazole, benzyladenine, benzylaminopurine, diphenylurea or kinetin), the gibberellins (e.g. $GA_3$, $GA_4$ or $GA_7$) and triapenthenol.

The following examples illustrate the invention. Throughout the examples, the term 'ether' refers to diethyl ether, magnesium sulphate was used to dry solutions, except where otherwise stated, and solutions were concentrated under reduced pressure. Reactions involving air- or water-sensitive intermediates were performed under an atmosphere of nitrogen and solvents were dried before use, where appropriate. Unless otherwise stated, chromatography was performed on a column of silica gel as the stationary phase. Where shown, NMR data are selective; no attempt is made to list every absorption in all cases. $^1$H NMR spectra were recorded using CDCl$_3$ solutions unless otherwise stated. The following abbreviations are used throughout:

DMF=N,N-dimethylformamide
d=doublet
NMR=nuclear magnetic resonance
m=multiplet
s=singlet
br=broad

EXAMPLE 1

This example illustrates the preparation of compound No. 127 of Table I (see Scheme I).

A solution of 3-trifluoromethylacetophenone oxime (1.59 g) in DMF (20 ml) was added dropwise to a stirred suspension of sodium hydride (0.187 g) in DMF (10 ml). An hour later, the reaction mixture was cooled to 0° C. and a solution of (E)-methyl 2-(bromomethyl)phenylglyoxylate O-methyloxime [(A), 2.36 g, prepared as described in EP-A-0363818] in DMF (20 ml) was added dropwise with stirring. After a further 3 hours, the reaction mixture was poured into water and extracted with ethyl acetate (x3). The organic extracts were washed with brine, dried, concentrated and chromatographed using ethyl acetate:hexane (1:4) as eluant to give the bis-oxime ether (B) (2.83 g, 88% yield) as a colourless gum; $^1$H NMR (270 MHz): δ2.21(3H,s), 3.82(3H,s), 4.03(3H,s), 5.15(2H,s), 7.1–7.9(8H,m) ppm.

A solution of the bis-oxime ether (B) (2.3 g) in methanol was added dropwise to a cooled, saturated solution of methylamine in methanol (200 ml). After standing for 2 days, the reaction mixture was concentrated and the residual yellow gum was chromatographed using ether:hexane (3:2) as eluant to give the title compound (1.46 g, 64% yield) as a clear gum; $^1$H NMR (270 MHz): δ2.22(3H,s), 2.88(3H,d), 3.94(3H,s), 5.14(2H,s), 6.74(1H,br m), 7.1–7.9(8H,m) ppm.

EXAMPLE 2

This example illustrates the isomerization of (Z)-methyl 2-methylphenylglyoxylate O-methyloxime to the corresponding (E)-isomer for use in the preparation of (E)-methyl 2-(bromomethyl)phenylglyoxylate O-methyloxime (A) in Example 1.

(Z)-Methyl 2-methylphenylglyoxylate O-methyloxime (102 mg) was dissolved in dioxane (5 ml) and concentrated hydrochloric acid (0.25 ml) was added. The reaction was heated to reflux for 24 hours and allowed to cool. The reaction was partitioned between ether and a saturated solution of sodium bicarbonate in water. The aqueous layer was extracted twice more with ether and the combined organic layers were dried (sodium sulphate) and concentrated. The residue was purified by flash chromatography (eluting with 25% ether in hexane) to give the title compound (42 mg, 41% yield); $^1$H NMR (270 MHz): δ2.2(3H,s), 3.85(3H,s), 4.05(3H,s), 7.1(1H,m), 7.2–7.4(3H,m) ppm.

The following are examples of compositions suitable for agricultural and horticultural purposes which can be formulated from the compounds of the invention. Such compositions form another aspect of the invention.

EXAMPLE 3

An emulsifiable concentrate is made up by mixing and stirring the ingredients until all are dissolved.

| | |
|---|---|
| Compound No. 260 of Table I | 10% |
| Benzyl alcohol | 30% |
| Calcium dodecylbenzenesulphonate | 5% |
| Nonylphenolethoxylate (13 mole ethylene oxide) | 10% |
| Alkyl benzenes | 45% |

EXAMPLE 4

The active ingredient is dissolved in methylene dichloride and the resultant liquid sprayed on to the granules of attapulgite clay. The solvent is then allowed to evaporate to produce a granular composition.

| | |
|---|---|
| Compound No. 264 of Table I | 5% |
| Attapulgite granules | 95% |

EXAMPLE 5

A composition suitable for use as a seed dressing is prepared by grinding and mixing the three ingredients.

| | |
|---|---|
| Compound No. 269 of Table I | 50% |
| Mineral oil | 2% |
| China clay | 48% |

EXAMPLE 6

A dustable powder is prepared by grinding and mixing the active ingredient with talc.

| | |
|---|---|
| Compound No. 295 of Table I | 5% |
| Talc | 95% |

EXAMPLE 7

A suspension concentrate is prepared by ball milling the ingredients to form an aqueous suspension of the ground mixture with water.

| | |
|---|---|
| Compound No. 330 of Table I | 40% |
| Sodium lignosulphonate | 10% |
| Bentonite clay | 1% |
| Water | 49% |

This formulation can be used as a spray by diluting into water or applied directly to seed.

EXAMPLE 8

A wettable powder formulation is made by mixing together and grinding the ingredients until all are thoroughly mixed.

| | |
|---|---|
| Compound No. 331 of Table I | 25% |
| Sodium lauryl sulphate | 2% |
| Sodium lignosulphonate | 5% |
| Silica | 25% |
| China clay | 43% |

EXAMPLE 9

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration immediately before use. The formulations (100 ppm active ingredient) were sprayed on to the foliage or applied to the roots of the plants in the soil. The sprays were applied to maximum retention and the root drenches to a final concentration equivalent to approximately 40 ppm a.i. in dry soil. Tween 20 was added to give a final concentration of 0.05% when the sprays were applied to cereals.

For most of the tests the compounds were applied to the soil (roots) or to the foliage (by spraying) one or two days before the plant was inoculated with the disease. Exceptions were the tests on *Puccinia recondita* amd on *Erysiphe graminis* in which the plants were inoculated 48 hours and 24 hours, respectively, before treatment. Foliar pathogens were applied by spray as zoosporangial suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease level present (i.e. leaf area covered by actively sporulating disease) on each of the treated plants was recorded using the following assessment scale:
0=0% disease present
20=10.1-20% disease present
1=0.1-1% disease present
30=20.1-30% disease present
3=1.1-3% disease present
60=30.1-60% disease present
5=3.1-5% disease present
90=60.1-100% disease present
10=5.1-10% disease present Each assessment was then expressed as a percentage of the level of disease present on the untreated control plants. This calculated value is referred to as a POCO (Percentage of Control) value. An example of a typical calculation is as follows:
Disease level on untreated control=90
Disease level on treated plant=30

$$POCO = \frac{\text{disease level on treated plant}}{\text{disease level on untreated control}} \times 100 = \frac{30}{90} \times 100 = 33.3$$

This calculated POCO value is then rounded to the nearest of the values in the 9-point assessment scale shown above. In this particular example, the POCO value would be rounded to 30. If the calculated POCO falls exactly mid-way between two of the points, it is rounded to the lower of the two values.

The results displayed in Table V below represent these rounded POCO values.

TABLE V

| Compound No of Table I | Pr | Egt | Sn | Po | Tc | Vi | Pv | Pil |
|---|---|---|---|---|---|---|---|---|
| 63 | 0 | 0 | 0 | 10 | — | 0 | 0 | 30 |
| 75 | 0$^a$ | 0$^a$ | 5$^a$ | 90$^a$ | — | 0$^a$ | 0$^a$ | 90$^a$ |
| 103 | 5$^a$ | 30$^a$ | 1$^a$ | 20$^a$ | — | 0$^a$ | 0$^a$ | 90$^a$ |
| 109 | 1$^a$ | 0$^a$ | 0$^a$ | 0$^a$ | — | 0$^a$ | 0$^a$ | 90$^a$ |
| 115 | 0 | 0 | 0 | 0 | — | 0 | 0 | 0 |
| 127 | 0* | 0 | 0 | 0 | 0 | 0 | 0 | 0 |
| 176 | 0 | 0 | 0 | 1 | — | 0 | 0 | 0 |
| 236 | 0 | 0 | 0 | 0 | 0 | 0 | 0 | 10 |
| 260 | 0* | 0 | 0 | 0 | 0 | 0 | 0 | 3 |
| 269 | 0* | 0 | 0 | 0 | 5 | 0 | 0 | 5 |
| 326 | 0 | 0 | 0 | 0 | — | 0 | 0 | 0 |
| 328 | 0 | 0 | 0 | 0 | 0 | 0 | 0 | 90 |
| 329 | 5$^a$ | 30$^a$ | 3$^a$ | 20$^a$ | 0$^a$ | 0$^a$ | | |
| 331 | 5$^a$ | 0$^a$ | 30$^a$ | 90$^a$ | — | 20$^a$ | 10$^a$ | 90$^a$ |
| 332 | 5$^a$ | 0$^a$ | 5$^a$ | 30$^a$ | — | 0$^a$ | 0$^a$ | 90$^a$ |
| 333 | 0 | 0 | 0 | 20 | — | 0 | 0 | 90 |
| 334 | 10$^a$ | 30$^a$ | 20$^a$ | 30$^a$ | — | 60$^a$ | 10$^a$ | 90$^a$ |
| 335 | 5$^a$ | 0$^a$ | 30$^a$ | 90$^a$ | — | 5$^a$ | 5$^a$ | 90$^a$ |
| 335A | 0 | 0 | 0 | 0 | — | 0 | 0 | 10 |
| 336 | 0 | 0 | 0 | 30 | — | 0 | 0 | 90 |
| 337 | 0 | 0 | 0 | 0 | 0 | 0 | 0 | 10 |

$^a$ = 10 ppm foliar application only
* = foliar protectant test (i.e. plant inoculated before treatment)
— = No result
Key to diseases
Pr *Puccinia recondita*
Egt *Erysiphe graminis tritici*
Sn *Septoria nodorum*
Po *Pyricularia oryzae*
Tc *Thanetophorus cucumeris*
Vi *Venturia inaequalis*
Pv *Plasmopara viticola*
Pil *Phytophthora infestans lycopersici*

CHEMICAL FORMULAE
(in description)

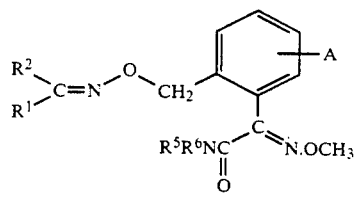

TABLE I (I)

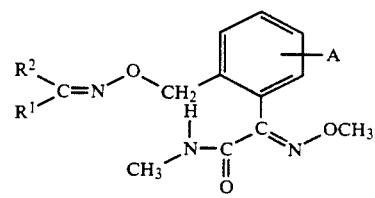

TABLE II (I.1)

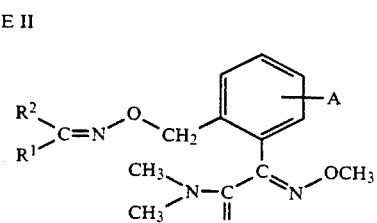

TABLE III (I.2)

(I.3)
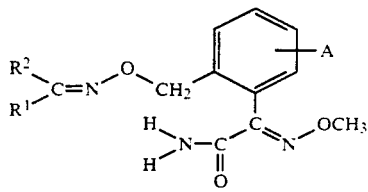
Compound 53 is:
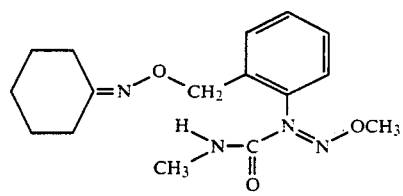
Compound 54 is:
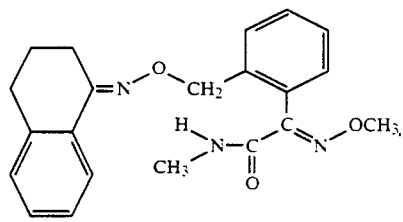
Compound 55 is:
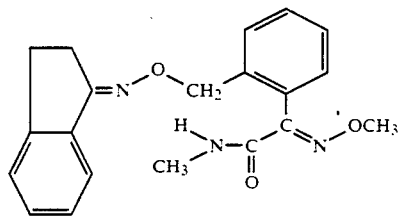
Compound 152 is:
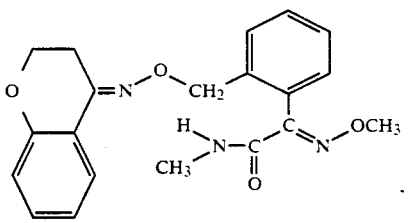
Compound 153 is:
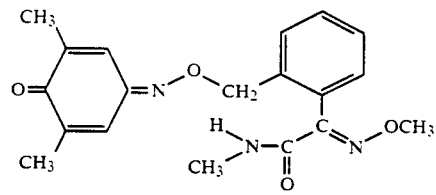
Compound 307 is
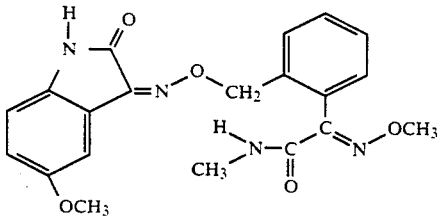
Compound 318 is
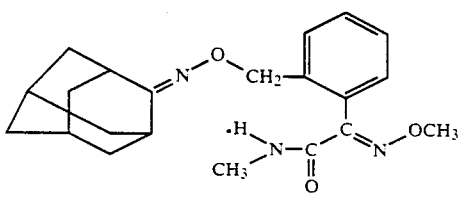
Compound 325 is
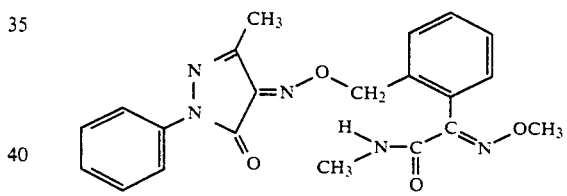
(II)
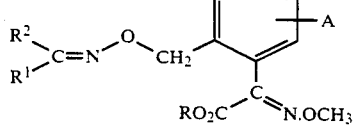
Scheme I
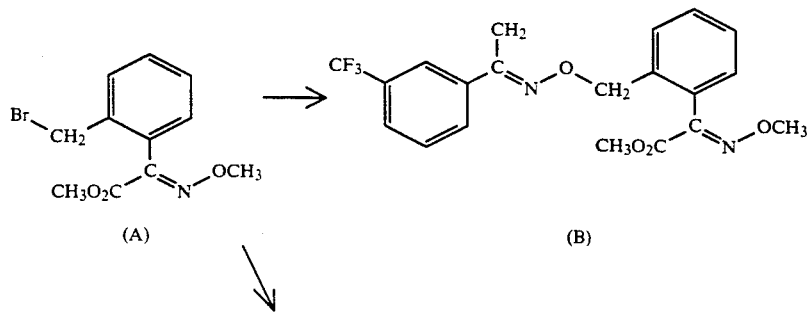
(A)    (B)

Scheme 1

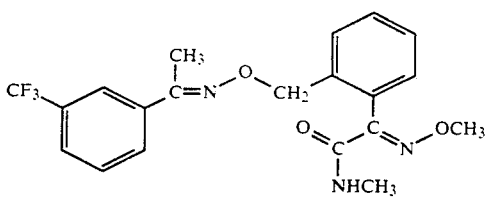

-continued

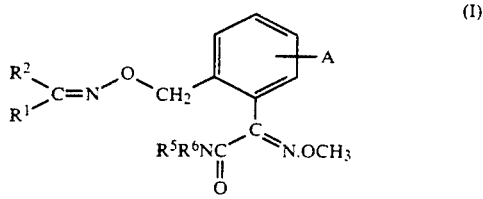

Compound 127 of Table I

We claim:

1. A compound having the formula (I):

(I)

and stereoisomers thereof, wherein A is hydrogen, halo, hydroxy, $C_{1-4}$ alkyl, $C_{1-4}$ alkoxy, $C_{1-4}$ haloalkyl, $C_{1-4}$ haloalkoxy, $C_{1-4}$ alkylcarbonyl, $C_{1-4}$ alkoxycarbonyl, phenoxy, nitro or cyano; $R_1$ and $R_2$, which may be the same or different, are hydrogen, optionally substituted alkyl, optionally substituted cycloalkyl, optionally substituted cycloalkylalkyl, optionally substituted aralkyl, optionally substituted aryloxyalkyl, optionally substituted alkenyl, optionally substituted alkynyl, optionally substituted alkoxy, optionally substituted aryl, optionally substituted aryloxy, nitro, halo, cyano, $-NR^3R^4$, $-CO_2R^3$, $-CONR^3R^4$, $-COR^3$, $-S(O)_nR^3$ wherein n is 0, 1 or 2, $(CH_2)_mPO(OR^3)_2$ wherein m is 0 or 1, or $R^1$ and $R^2$ join to form a carbocyclic ring system; $R^3$ and $R^4$, which are the same or different, are hydrogen, optionally substituted alkyl, optionally substituted aralkyl, optionally substituted alkenyl, optionally substituted alkynyl or optionally substituted aryl; and $R^5$ and $R^6$ are independently hydrogen or $C_{1-4}$ alkyl.

2. A compound according to claim 1 wherein alkyl and alkoxy moieties are optionally substituted with halo, cyano, hydroxy, $C_{1-4}$ alkoxy or $C_{1-4}$ alkoxy($C_{1-4}$) alkoxy; cycloalkyl moieties are optionally substituted with halo, hydroxy or $C_{1-4}$ alkoxy; alkenyl moieties are optionally substituted with optionally substituted aryl; alkynyl moieties are optionally substituted with optionally substituted aryl; and aryl moieties are optionally substituted with one or more of the following: halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkenyloxy, $C_{2-4}$ alkynyloxy, halo($C_{1-4}$)alkyl, halo($C_{1-4}$)alkoxy, $C_{1-4}$ alkylthio, hydroxy($C_{1-4}$)-alkyl, $C_{1-4}$ alkoxy($C_{1-4}$)alkyl, $C_{1-4}$ alkoxy($C_{1-4}$)alkoxy, $C_{3-6}$ cycloalkyl, $C_{3-6}$ cycloalkyl($C_{1-4}$)alkyl, optionally substituted aryl, optionally substituted aryloxy, optionally substituted aryl($C_{1-4}$)alkyl, in which the alkyl moiety is optionally substituted with hydroxy, optionally substituted aryl($C_{2-4}$)alkenyl, optionally substituted aryl($C_{1-4}$)alkoxy, optionally substituted aryloxy($C_{1-4}$)alkyl, acyloxy, cyano, isocyano, thiocyanato, isothiocyanato, nitro, $-NR'R''$, $-NH-COR'$, $-NHCONR'R''$, $-CONR'R''$, $-COOR'$, $-SO_2R'$, $-OSO_2R$, $-COR'$, $-CR'=NR''$ or $-N=CR'R''$ in which R' and R'' are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl, these phenyl and benzyl groups being optionally substituted with halogen, $C_{1-4}$ alkyl or $C_{1-4}$ alkoxy; and the aryl rings of any of the other foregoing substituents being optionally substituted with one or more of the following: halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$)alkoxy, $C_{1-4}$ alkylthio, hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, alkanoyloxy, benzoyloxy, cyano, isocyano, thiocyanato, isocyanato, nitro, $-NR'R''$, $-NHCOR'$, $-NHCONR'R''$, $-CONR'R''$, $-COOR'$, $-SO_2R'$, $-OSO_2R'$, $-COR'$, $-CR'=NR''$ or $-N=CR'R''$ in which R' and R'' have the meanings given above.

3. A compound according to claim 1 wherein A is hydrogen, halo, hydroxy, methyl, methoxy, trifluoromethyl, trifluoromethoxy, $C_{1-2}$ alkylcarbonyl, $C_{1-2}$ alkoxycarbonyl, phenoxy, nitro or cyano; $R^1$ is $C_{1-4}$ alkyl, halo($C_{1-4}$)alkyl, $C_{1-4}$ alkoxy, halo($C_{1-4}$)alkoxy, $C_{1-4}$ alkylcarbonyl, $C_{1-4}$ alkoxycarbonyl, cyano, phenyl($C_{1-4}$)alkyl, or phenyl, the phenyl moieties of any of the foregoing being optionally substituted with one or more of halo, hydroxy, $C_{1-4}$ alkyl, halo($C_{1-4}$)alkyl, $C_{1-4}$ alkoxy, halo($C_{1-4}$)alkoxy, $C_{1-4}$ alkylcarbonyl, $C_{1-4}$ alkoxycarbonyl, nitro, cyano, phenyl, phenoxy, benzyl or benzyloxy; and $R^2$ is hydrogen, halo, $C_{1-4}$ alkyl, halo($C_{1-4}$)alkyl, $C_{1-4}$ alkylcarbonyl, $C_{1-4}$ alkoxycarbonyl, cyano or phenyl; or $R^1$ and $R^2$ join together to form a $C_{5-10}$ carbocyclic ring system.

4. A compound according to claim 1 wherein A is hydrogen or halo; $R^1$ is $C_{1-4}$ alkyl, benzyl, $C_{1-4}$ alkylcarbonyl, $C_{1-4}$ alkoxycarbonyl, cyano or phenyl, the phenyl moieties of any of the foregoing being optionally substituted with one or more of halo, $C_{1-4}$ alkyl, trifluoromethyl, $C_{1-4}$ alkoxy, trifluoromethoxy, nitro, cyano, phenyl or benzyloxy; and $R^2$ is hydrogen, $C_{1-4}$ alkyl, $C_{1-4}$ alkylcarbonyl, $C_{1-4}$ alkoxycarbonyl, cyano or phenyl; or $R^1$ and $R^2$ join together to form a cyclopentyl or cyclohexyl ring to which is optionally fused a benzene ring; and $R^5$ and $R^6$ are independently hydrogen or $C_{1-4}$ alkyl.

5. A compound according to claim 1 wherein A is hydrogen; $R^1$ is phenyl, optionally substituted with one or more of halo, $C_{1-6}$ alkyl, halo($C_{1-4}$)alkyl, $C_{1-6}$ alkoxy, cyano($C_{1-4}$)alkoxy, halo($C_{1-4}$)alkoxy, $C_{1-4}$ alkoxy($C_{1-4}$)alkyl, $C_{1-4}$ alkoxy($C_{1-4}$)alkoxy, $C_{1-4}$alkoxy($C_{1-4}$)alkoxy($C_{1-4}$)alkoxy, $C_{1-6}$ alkylthio, $C_{2-6}$ alkenyl, $C_{2-6}$ alkenyloxy, $C_{2-6}$ alkynyl, $C_{2-6}$ alkynyloxy, nitro, cyano, phenyl, phenoxy, benzyloxy, $CO_2R'$, $CONR'R''$, $CSNR'R''$, $NR'R''$, $S(O)_nR'$, $NHCONR'R''$, in which R' and R'' are independently H or $C_{1-4}$ alkyl and n is 0, 1 or 2; $R^2$ is methyl; $R^5$ is hydrogen and $R^6$ is methyl; or where appropriate, the N-oxide thereof.

6. A fungicidal composition comprising, as an active ingredient, a compound as defined in claim 1 and a fungicidally acceptable carrier or diluent thereof.

7. A process for combating fungi which comprises applying to plants or seeds, or to their locus, a compound as claimed in claim 1.

* * * * *